United States Patent [19]
Mathiowitz et al.

[11] Patent Number: 5,271,961
[45] Date of Patent: Dec. 21, 1993

[54] METHOD FOR PRODUCING PROTEIN MICROSPHERES

[75] Inventors: Edith Mathiowitz, Brookline; Howard Bernstein, Cambridge; Eric Morrel, Needham; Kirsten Schwaller, Duxbury, all of Mass.

[73] Assignee: Alkermes Controlled Therapeutics, Inc., Cambridge, Mass.

[21] Appl. No.: 902,505

[22] Filed: Jun. 23, 1992

Related U.S. Application Data

[63] Continuation of Ser. No. 557,551, Jul. 24, 1990, abandoned, which is a continuation-in-part of Ser. No. 432,785, Nov. 6, 1989, abandoned.

[51] Int. Cl.$^5$ .............. B01J 13/12; A61K 9/16; A61K 9/52; A61K 9/54
[52] U.S. Cl. .............. 427/213.31; 427/213.3; 427/213.36; 424/491; 424/499; 426/96
[58] Field of Search .......... 427/213.36, 213.3, 213.31; 264/4.6; 426/96; 424/491, 499

[56] References Cited

U.S. PATENT DOCUMENTS

| | | | |
|---|---|---|---|
| 3,092,553 | 6/1963 | Fisher, Jr. et al. | 264/4.4 X |
| 3,116,206 | 12/1963 | Brynko et al. | 427/213.3 X |
| 3,937,668 | 2/1976 | Zolle | 264/4.3 |
| 3,943,063 | 3/1976 | Morishita et al. | 427/213.36 |
| 4,107,288 | 8/1978 | Oppenheim et al. | 427/213.3 X |
| 4,194,013 | 3/1980 | Rehacek et al. | 427/213.3 X |
| 4,420,442 | 12/1983 | Sands | 264/13 |
| 4,818,542 | 4/1989 | DeLuca et al. | 424/491 |
| 4,876,094 | 10/1989 | Benton | 424/491 |
| 4,940,588 | 8/1990 | Sparks et al. | 424/490 |
| 4,952,402 | 8/1990 | Sparks et al. | 424/497 X |
| 5,021,248 | 6/1991 | Stark et al. | 426/96 |

FOREIGN PATENT DOCUMENTS

| | | |
|---|---|---|
| 0000667 | 3/1979 | European Pat. Off. |
| WO90/03123 | 4/1990 | PCT Int'l Appl. |
| 2166651 | 5/1986 | United Kingdom |
| 2224258A | 5/1990 | United Kingdom |

OTHER PUBLICATIONS

Sato et al., *Pharmaceutical Research*, vol. 5, No. 1, "Porous Biodegradable Microspheres . . . " (1988).
Tice, et al., *J. Controlled Rel.* 2, 343–352 (1985).
Suzuki, et al., *Pharm. Soc. Jap. Chem. Pharm. Bull.* 37 (4), 1051–1054 (1989).

*Primary Examiner*—Robert L. Stoll
*Assistant Examiner*—John M. Covert
*Attorney, Agent, or Firm*—Kilpatrick & Cody

[57] ABSTRACT

Protein microspheres are formed by phase separation in a non-solvent followed by solvent removal. The preferred proteins are prolamines, such as zein, that are hydrophobic, biodegradable, and can be modified proteolytically or chemically to endow them with desirable properties, such as a selected degradation rate. Composite microspheres can be prepared from a mixture of proteins or a mixture of proteins with one or more bioerodible polymeric materials, such as polylactides. Protein coatings can also be made. Compounds are readily incorporated into the microspheres for subsequent release. The process does not involve agents which degrade most labile proteins. The microspheres have a range of sizes and multiple applications, including drug delivery and delayed release of pesticides, fertilizers, and agents for environmental cleanup. Selection of microsphere size in the range of less than five microns and mode of administration can be used to target the microparticles to the cells of the reticuloendothelial system, or to the mucosal membranes of the mouth or gastrointestinal tract. Larger implants formed from the microspheres can also be utilized, especially for agricultural applications.

20 Claims, 3 Drawing Sheets

METHOD FOR PRODUCING PROTEIN MICROSPHERES

BACKGROUND OF THE INVENTION

This is a continuation of copending application Ser. No. 07/557,51, filed on Jul. 24, 1990, which is a continuation-in-part of U.S. Ser. No. 07/432,785, now abandoned, entitled "Method for Producing Protein Particles and Coatings" filed Nov. 6, 1989 by Edith Mathiowitz, Howard Bernstein, Eric Morrel and Kirsten Schwaller.

A number of processes have been utilized to make microspheres and microcapsules for a variety of applications. Most microspheres are made of synthetic polymers, such as poly(lactic acid) or polyorthoesters, and are formed by solvent evaporation, spray drying, or phase separation. When the microspheres or microcapsules are used for drug delivery, the process must yield a product that is small, consistent in size and drug distribution, and with controlled degradation properties.

Proteins have also been used to form microparticles or microspheres for drug delivery. R. C. Oppenheim, *Polymeric Nanoparticles and Microspheres* Guiot and Couvreur, editors, chapter 1, pp. 1-25 (CRC Press, 1986), reviews formation, properties and drug delivery using proteins. Most are crosslinked in solution using glutaraldehyde, or hardened at elevated temperatures. Unfortunately, there are problems with significant loss of biological activity of incorporated materials and lack of controlled size and in vivo degradation rates. For example, zein microspheres prepared as carriers for chemotherapeutic agents by crosslinking a zein solution containing the drug, as reported by Suzuki, et al., *Chem. Pharm. Bull.* 37(4), 1051-1054 (1989), were quite heterogeneous in size, and displayed incorporation of less than 30% of the drug. This same group reported in *Chem. Pharm. Bull.* 37, 757-759 (1989), that yield and size range were improved by addition of a catalytic amount of dl-camphorsulfonic acid and rapid addition of polyvinylpyrrolidone, a surfactant and binder. Incorporation of drug was still less than 35%, however. PCTUS87/02025 by Clinical Technologies Associates, Inc., reports the preparation and use for drug delivery of microspheres made of "protenoids", thermal condensation polymers of mixed amino acids. While these materials have useful properties, they are designed for specific applications and targeted release as a function of pH.

In a similar process, proteins have been used to make glutaraldehyde crosslinked beads incorporating bacteria for agricultural applications.

Proteins have also been used to make implants for drug delivery, as well as coatings and plasticizers for drug-containing polymeric microcapsules. For example, EPO 158277 to Hoechst AG describes an implantable preparation for the controlled release of a peptide, buserelin, using zein as the carrier, formed by dissolving the peptide and the zein in alcohol, spray drying and shaping the resulting mixture. EPO 077956 to Tanabe Seiyaku Ltd. describes the use of zein and other proteins as enteric coatings for microcapsules, formed using standard techniques for coating, i.e., spray coating or dipping. JP 80137936 to Sumitomo Chemical KK references the use of zein and other proteins and materials as plasticizers in ethylcellulose and methylcellulose microcapsules.

None of these methods of producing protein drug delivery devices can be used to incorporate high percentages of biologically active substances, especially labile substances, into uniform microspheres small enough to pass directly into the bloodstream when delivered orally, or with consistent release rates and sizes. None of the other processes yield a material having no binder or crosslinking agent present, that consists only of the natural protein.

It is therefore an object of the present invention to provide a method for making biodegradable protein microspheres that can be used for controlled or targeted drug delivery, systemically or topically, especially for delivery of labile substances and hydrophobic compounds, and the products thereof.

It is another object of the present invention to provide biodegradable protein microspheres for use as diagnostic agents and in radioimaging.

It is yet another object of the present invention to provide a method for making a delivery system for controlled, delayed release of agents into the environment, including enzymes, hormones, pesticides, and fertilizers, and the products thereof.

SUMMARY OF THE INVENTION

Protein microspheres are formed by phase separation in a non-solvent followed by solvent removal by extraction or evaporation. The preferred proteins are prolamines, such as zein, that are hydrophobic and biodegradable, which metabolize in the body to peptides and/or amino acids, and can be readily modified proteolytically or chemically, e.g., cross-linked or derivatized, to endow them with desirable properties, such as a selected degradation rate. Microspheres can be prepared from a mixture of proteins or a mixture of proteins with one more bioerodible synthetic polymeric materials, such as polylactides, as can protein coatings. Advantages to the process for forming the microspheres include the use of low temperatures, usually less than 45° C., and the absence of crosslinking agents such as glutaraldehyde.

Compounds are readily incorporated into the microspheres for subsequent release. The microspheres can be formed in a range of sizes for multiple applications, including drug delivery and delayed release of pesticides, fertilizers, and agents for environmental cleanup. Drug delivery can be achieved topically or systemically. Selection of microsphere size in the range of less than five microns and mode of administration can be used to target the microparticles to the cells of the reticuloendothelial system, or to the mucosal membranes of the mouth or gastrointestinal tract. Larger implants formed from the microspheres can also be utilized, especially for agricultural applications.

BRIEF DESCRIPTION OF THE DRAWINGS

FIGS. 2A and 2B are graphs of the % cumulative release of insulin into PBS over time in hours for microspheres; FIG. 2A: zein (17% w/w insulin) ([-]); Z-C6 (dark []); Z-C8 ([]); Z-C10 (dark ∆); Z-C12 (∆); FIG. 2B: deamidated zein ([-]); deamidated zein (DA-Z)-C6 (dark <>); DA-Z-C8 (dark [ ]); DA-Z-C10 (<>); DA-Z-C12 (dark [ ]).

DETAILED DESCRIPTION OF THE INVENTION

As used herein, "micro" refers to a particle having a diameter of from nanometers to micrometers. Microspheres are solid spherical particles; microparticles are particles of irregular or non-spherical shape. A microsphere may have an outer coating of a different composition than the material originally used to form the microsphere. Unless otherwise noted, the term microsphere can be used to encompass microcapsules and the term microparticles can be used to encompass microparticles, microspheres, and microcapsules. A "composite microsphere" is a microsphere formed of at least two different materials, either a protein and a polymer or two proteins. A "composite" is an aggregation of microspheres made as described herein, bound by materials known to those skilled in the art for this purpose.

Using the method described herein, protein microspheres are prepared by a phase separation, solvent removal process. The formation of the microspheres depends upon the differential solubility of proteins in water-miscible organic solvents, salt solutions, or acidic or basic solutions, as compared to their solubility in an immiscible phase, such as a nonpolar organic solvent or an oil. Most proteins are not soluble in oils. Accordingly, protein is dissolved in a first solvent which is a water-miscible organic, organic/aqueous, or binary organic solvent, acid, base or salt solution (the encapsulating phase). The compound to be incorporated, in the form of a suspension, emulsion, solution or particles, is added to the protein solution. This mixture is then contacted with a second liquid phase (the continuous phase) which does not dissolve the proteins and has limited miscibility with the first solvent. The continuous phase is preferably an oil, such as vegetable oil, silicone oil or mineral oil. Vigorous agitation is applied, and the first solvent is removed under conditions sufficient to form microspheres, usually by evaporation or extraction.

Coatings can also be made onto microparticles made of protein or non-protein polymers. To make the coatings, (1) protein is first dissolved in a solvent; (2) the particles or microparticles to be coated are added to the solution; (3) the protein/microparticle mixture is added to a second liquid phase which is immiscible with the first solvent and a non-solvent for the protein coating; (4) the mixture is agitated; and (5) the first solvent is removed (usually by evaporation or extraction) under conditions sufficient to cause the particles or microparticles to be coated with a protein coating.

The process described herein yields protein microspheres having a diameter of between nanometers and micrometers, with an average diameter between 0.01 micron to less than about 100 microns, having incorporated therein a compound to be delivered or released at a desired time and/or site. In the preferred method, the microspheres are stored frozen to enhance the stability of incorporated compounds over extended periods of time.

Composites containing the protein microspheres can be formed using standard techniques to encapsulate the protein microspheres in a polymer, either degradable or non-degradable, natural or synthetic. These materials are known to those skilled in the art. The protein microspheres can also be compressed or shaped by other techniques known to those skilled in the art.

Proteins Useful for Forming the Microspheres

In the preferred embodiments, the proteins are hydrophobic proteins such as prolamines, preferably zein. As used herein, proteins can be a single type of protein, a combination of proteins, or a combination of protein with polymer. Proteins are used to make the microspheres since they are natural, offer a diversity of properties and are degraded in vivo into innocuous amino acids or small peptides. Hydrophobic proteins have limited solubility in water and are soluble in organic solvents, aqueous mixtures of organic solvents, and binary mixtures of organic solvents. Examples of other useful proteins besides prolamines are collagen, casein, and keratin.

Prolamines are characterized by having a large number of hydrophobic-amino acids, such as glutamine, asparagine and proline. Prolamines are water-insoluble, but are soluble in many organic solvents, particularly alcohols, containing at least 1% water, but no more than 60% water, or a polar organic solvent.

Prolamines are readily available and inexpensive, for example, as the by-products of grain processing. Representative prolamines include gliadin, kafirin, zein and hordein. A preferred prolamine for use in making microspheres is zein. Both commercially available grades and purified forms of zein can be used. The properties of zein are described in detail by L. C. Swallen in: "Zein—A New Industrial Protein", *Ind. and Eng. Chem.*, 33:394-398 (1941).

Solvents for the Proteins Used to Form the Microspheres

The protein is dissolved in an appropriate solvent. The protein is "soluble" if more than 0.5% (w/v) of the protein dissolves in the solvent to form a visually transparent solution at room temperature (about 20°-25° C.). Prolamines are soluble, for example, in alcohols (ethanol), some ketones (e.g., methyl ethyl ketone, acetone) and amide solvents (e.g., acetamide), containing between 5% and 60% water; in extremely high (e.g., pH 10 or greater) or extremely low (pH 2 or less) pH solutions; and in aqueous solutions of from about 1.0 to about 6N inorganic salts (e.g., NaCl, KBr). Many binary solvent systems for zein are known, in which the primary components are polyols, especially lower aliphatic alcohols, ketones, or glycols, and the secondary components are water, aromatic hydrocarbons, halogenated hydrocarbons, especially chlorinated hydrocarbons, nitroparaffins, aldehydes and cyclic ethers. Specific examples include mixtures of alcohols and halogenated hydrocarbons and mixtures of alcohols and propylene glycol with ethylene glycol. Binary solvent systems for prolamines such as zein are reported by Manley and Evans, *Industrial and Engineering Chemistry* 36, 661-665 (1943).

Suitable Materials for the Continuous Phase

The compound to be incorporated is added to the protein solution. The compound can be in the form of a suspension, solution (in oil, organic solvent or water), emulsion, or particles. The compound/protein mixture is then introduced into a second liquid phase, the continuous phase, which (1) is immiscible or of limited miscibility with the protein solvent and (2) does not dissolve the protein. Solvents are "immiscible" if they will not mix with each other to form a stable homogeneous solution at the operating temperature without mixing. Immiscible phases tend to form separate layers under these conditions. Oils such as mineral oil, silicone oil, or vegetable oil are useful immiscible phases. Others include hexane, heptane, dodecane, and high boiling point petroleum ether.

One or more surfactants can be added to the protein/first solvent mixture or to the continuous phase to reduce the size of the protein microspheres. Suitable surfactants, and methods of use thereof, are known to those skilled in the art.

PROCESS FOR FORMING THE MICROSPHERES

The protein solution was added to the continuous phase, the mixture vigorously agitated, and the first solvent is removed, for example, preferably by evaporation, or by solvent extraction, under conditions forming microspheres. Efficient mixing can be achieved by fast mechanical stirring using a homogenizer and/or by using a baffled reactor to prevent laminar flow. If necessary, the mixture can be heated to a temperature of from between 22° C. and about 45° C. for a period of between about 15 minutes to 45 minutes. If heated, the mixture is first cooled to room temperature, then the microspheres incorporating the compound are washed, separated from the mixture, and dried. If the hydrophilic drug incorporated is unstable in aqueous media, the microspheres can be lyophilized.

In an alternative embodiment used when hydrophilic compounds are to be incorporated into the microspheres other than as particulates, a double emulsion technique is employed. For example, the compound to be incorporated is first dissolved in an aqueous solution. The zein is dissolved in a suitable binary organic mixture with low aqueous miscibility. Many binary organic solvents for zein are known, for example, mixtures of an alcohol, such as methanol, ethanol or isopropanol, with a halogenated hydrocarbon, with the halogenated hydrocarbon as the primary component. The aqueous solution is added to the organic solution of zein and a water in oil emulsion is created. This emulsion is then added to a second organic liquid phase, the continuous phase, which is immiscible or of limited miscibility with the organic solvent for zein, such as an oil, to form a double water in oil emulsion. This solvent is then removed, as described previously, to form microspheres.

Modification of the Microspheres

The properties of the microspheres can be modified for a given application, for example, by chemically and/or enzymatically altering the starting protein prior to forming the microspheres. Such modifications can produce a protein having enhanced or altered thermal stability, surface reactivity, lipophilicity, molecular weight, charge, shear stability and resistance to proteases.

Enzymatic Modification of the Protein

The functionality, surface properties and molecular weight distribution of the protein can be modified by enzymatic treatment. For example, enzymatic hydrolysis of zein, having a dimer molecular weight of about 38,000 daltons, in 90% ethanol using a protease, such a papain or chymotrypsin, yields polypeptides with a molecular weight of about 1,000 daltons which retain the solubility characteristics of the intact protein, i.e., the polypeptides are still insoluble in water but soluble in 90% ethanol. The degree of hydrolysis can be controlled by varying the amount of enzyme used or the reaction time during which the protein is exposed to the enzyme.

The stability of the protein can be enhanced by crosslinking the protein prior to use in the phase separation process by the addition of an enzyme which catalyzes intra- and/or intermolecular crosslinking of the protein, such as transglutaminase, or protein disulfide isomerase. Transglutaminase and protein disulfide isomerase cause inter- and intramolecular crosslinking of the protein through the amino acids glutamine and cysteine, respectively. Transglutaminase catalyzes an acyl transfer reaction, in which the amide group of the amino acid glutamine is the acyl donor. Other enzymatic processes are known which alter the properties of proteins, before or after formation of the microspheres.

Chemical Modification of the Protein

The properties of the microspheres can also be altered by chemical modification of the proteins used in their preparation, either before or after formation of the microspheres. Such modifications can include treating the proteins with an acid, base or other agent which alters the structure of one or more amino acid side chains, which in turn alters the character of the protein. For example, the high glutamine and asparagine content of prolamines, particularly zein, provides a means for manipulating the charge characteristics of the protein, and therefore the hydrophobicity, by deamidation. The preferred deamidation method involves mild acid-catalyzed deamidation (at a pH of about 1) at elevated temperatures (between 25° C. and 65° C.) for a period of time sufficient to accomplish the desired level of deamidation. The deamidation process may be followed by measuring the release of ammonia with an ammonia electrode. Deamidation can be terminated by the addition of ammonium carbonate or other base.

Other examples of chemical modification include esterification of the protein with fatty alcohols, or acylation of the protein with fatty anhydrides, which can alter the acid (or base) sensitivity of the protein product. For example, zein or zein peptides can be deamidated as described above, then the deamidated zein reacted with a fatty acid to form the fatty acid ester of the protein. Non-deamidated or deamidated zein peptides can also be reacted with fatty alcohols to form fatty acylated zein or zein peptides. These fatty acid-modified proteins or peptides can then be used as starting material to form the microspheres.

The charge on the protein can also be modified by crosslinking amino acids or polyamino acids to the protein, using glutaraldehyde or carbodiimide.

Proteins can be modified before or after formation of the microspheres. However, an advantage of the phase separation process is that harsh chemical or heat treatment of the protein after formation of the microspheres is not required. Accordingly, when modification of the protein using agents such as glutaraldehyde for crosslinking of the protein is desirable, the protein is treated prior to incorporation of the compound to be delivered and formation of the microspheres.

Formulation of Protein-Polymer Microspheres

Proteins can be combined with non-protein polymers to form composite microspheres. Bioerodible synthetic or natural polymers are preferred. The term "bioerodible", or "biodegradable", as used herein refers to materials which are enzymatically or chemically degraded in vivo into simpler chemical species. An example of a natural polymer are polysaccharides. Synthetic polymers which degrade in vivo into innocuous products include poly(lactic acid) (PLA), poly(glycolic acid) (PGA) and co-polymers of PLA and PGA, polyorthoesters, polyanhydrides, polyphosphazene, polycaprolactone, polyhydroxybutyrate, blends and copolymers thereof.

PLA, PGA and PLA/PGA copolymers are particularly useful for forming prolamine composite microspheres. PLA polymers are usually prepared from the cyclic esters of lactic acids. Both L(+) and D(−) forms of lactic acid can be used to prepare the PLA polymers, as well as the optically inactive DL-lactic acid mixture of mixtures of D(−) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. Nos. 1,995,970 to Dorough; 2,703,316 to Schneider; 2,758,987 to Salzberg; 2,951,828 to Zeile; 2,676,945 to Higgins; and 2,683,136; 3,531,561 to Trehu.

PGA is the homopolymer of glycolic acid (hydroxyacetic acid). In the conversion of glycolic acid to poly(glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture", *Chemistry and Industry*, 905 (1970).

Both the release of the incorporated compound and the bioerosion of the matrix are related to the molecular weights of PLA, PGA or PLA/PGA. The higher molecular weights, weight average molecular weights of 90,000 or higher, result in polymer matrices which retain their structural integrity for longer periods of time; while lower molecular weights, weight average molecular weights of 30,000 or less, result in both slower release and shorter matrix lives.

Matrices made of either a protein mixture or a protein-polymer mixture, such as prolamine/PLA, prolamine/PGA or prolamine/PLA-PGA, can be designed with a variety of degradation and diffusion rates. In general, degradation is a function of the protein and polymer composition. Diffusion is a function of the matrix composition, form, and the nature of the incorporated material. Matrices can be synthesized to degrade over periods of time shorter than, equal to or longer than the period of release of incorporated compound. The compound can be released by diffusion, degradation of matrix, or a combination of diffusion through the matrix and release as the matrix degrades.

These composite matrices can take one of several forms: protein microspheres with a polymer coating; polymer microparticles or microcapsules encapsulated by protein; bioactive compounds and protein microspheres encapsulated by polymer; or protein microspheres with or without incorporated bioactive compound and bioactive compound encapsulated by polymer.

Compounds Which Can Be Incorporated

Both hydrophobic and hydrophilic compounds can be incorporated into the microspheres. Hydrophobic compounds can usually be co-solubilized in the aqueous/organic phase solution with the protein. Hydrophilic compounds are usually dispersed in the protein solution as particulates, although the double emulsion process or binary solvent systems described above can be used to solubilize the compounds. The use of particulates results in a higher burst of compound being released initially, as compared to when the compound is solubilized in the protein solution.

For drug delivery, biologically active agents having therapeutic, prophylactic or diagnostic activities can be delivered. These can be organic or inorganic compounds, proteins, or a wide variety of other compounds, including nutritional agents such as vitamins, minerals, amino acids and fats. Examples of agents include hormones, antigens, antibiotics, steroids, decongestants, neuroactive agents, and anesthetics or sedatives. The agents can be in various forms, such as unchanged molecules, components of molecular complexes, or pharmacologically acceptable salts, such as hydrochloride, hydrobromide, sulfate, phosphate, nitrate, borate, acetate, maleate, tartrate and salicylate. For acidic drugs, salts of metals, amines or organic cations (e.g., quaternary ammonium) can be used. Simple derivatives of the drugs (such as ethers, esters, and amides), which have desirable retention and release characteristics, can also be used.

Imaging agents including metals, radioactive isotopes, radiopaque agents such as barium, and radiolucent agents, including air, can also be incorporated. Air can be encapsulated by sonicating or agitating the protein solution before making the microspheres. The microspheres containing air filled voids are useful for radioimagery.

Various other non-biologically active agents such as colors, flavorings and fragrances can also be incorporated, alone or in combination with the biologically active agents.

Other compounds that can be incorporated include pesticides, fertilizers, pheremones, and agents used in environmental cleanup (including bacteria, chelating agents, and enzymes such as lipases and proteases).

The amount of compound incorporated in the delivery device varies widely depending on the particular agent, the desired effect and the time span over which it takes the matrix to release the compound. The upper and lower limits on the amount of the compound to be incorporated into the device can be determined empirically by comparing microspheres containing a range of compound.

Sizes of Microsheres Produced by Method

The microspheres can be produced in a variety of sizes, ranging from nanometer-sized microparticles up to an average particle size of about 100 microns. Microspheres having an average particle size of from about 50 to 100 nm to about 20 microns are more preferred. Microspheres having an average particle size of from about 100 nm to about 5 microns are particularly preferred for use in drug delivery because microspheres in this size range may be absorbed into the bloodstream and/or lymphatic system or phagocytized.

Figure 1A:
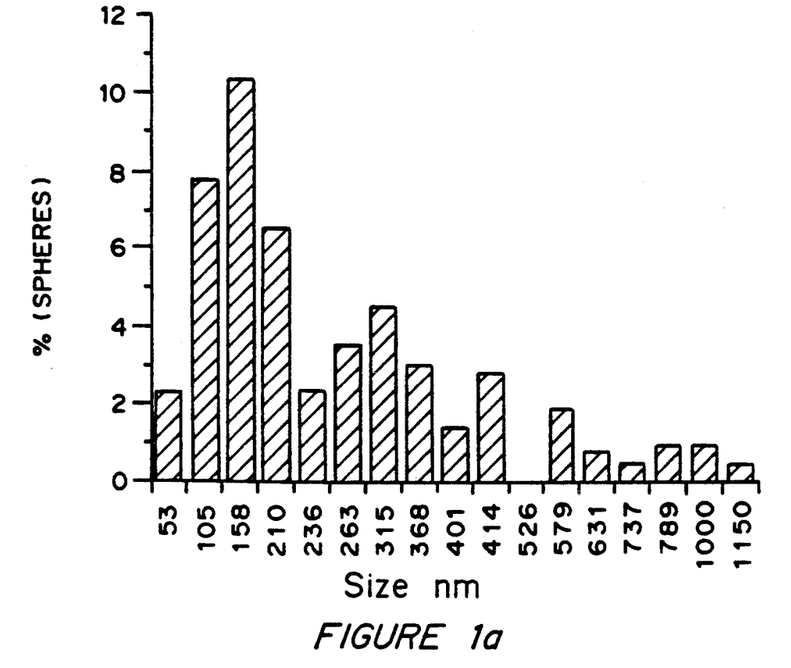
FIGS. 1A and 1B are the percent size distribution of particles having diameters in the nanometer range (FIG. 1A) and micrometer range (FIG. 1B).
Figure 1B:
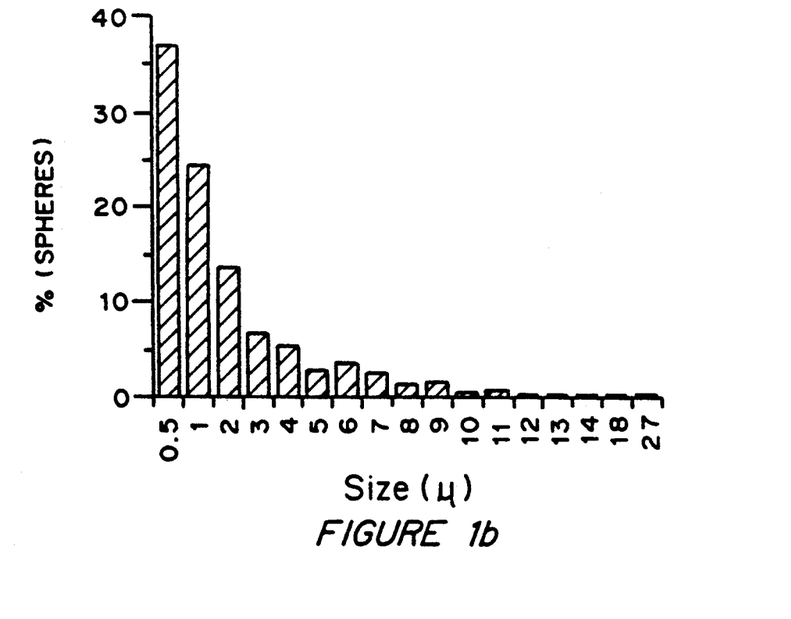

The size and other characteristics of the microspheres can be determined using scanning electron microscopy, (SEM), light scattering and differential scanning calorimetry (DSC). The size ranges of microspheres produced by this method are shown in FIGS. 1A and 1B.

Preparation of Protein Coatings

Protein coatings are made using a variation of the method to make microspheres. Particles (including particles of non-uniform shape, microspheres and microcapsules) to be coated can be made from any polymeric substance, usually non-protein substances or modified proteins, or simply material to be released. To form the coating, the protein is dissolved, the particles to be coated added, and the protein/microparticle mixture added to the continuous phase, the mixture agitated and the solvent removed, preferably by evaporation, or by solvent extraction, under conditions causing the particles to be coated with a protein coating.

Preparation of Composites of the Microspheres

The microspheres, either formed entirely of protein, or of protein in combination with polymer, or coated with protein, alone or in combination with bioactive agents, can be shaped into composites using techniques known to those skilled in the art. The preferred method is to compress the microspheres in a mold. Binders or surfactants can be added to facilitate formation of the composite. The microspheres can also be cast in a polymer solution which solidifies upon removal of the solvent or a decrease in temperature.

The present method provides unique protein microspheres and protein coatings, particularly for drug delivery applications. The method reproducibly and efficiently produces protein microspheres of a uniform size, or a range of diameters. The method has considerable flexibility in producing microspheres having desired characteristics, such as a desired diameter or size distribution, release rate or degradation rate. In addition, the method produces stable microspheres, with efficient incorporation of biologically active compounds, e.g., greater than 90% incorporation, in most cases. The microspheres and coatings are safe, non-toxic and degrade in vivo to amino acids or small peptides. The method can also be used to provide a protective non-toxic protein coating on a substrate. The methods, and products thereof, are further described with reference to specific non-limiting embodiments.

EXAMPLE 1

Preparation of Prolamine Microspheres Containing Particles of Insulin, a Protein In a preferred embodiment of the present method, a suspension of prolamine microspheres is produced by dissolving the prolamine in the first solvent, 90% ethanol, to form the encapsulating phase, adding the compound to be incorporated, and agitating the mixture to disperse the prolamine solution into an immiscible continuous phase, corn oil. The first solvent is then removed by evaporation at a preferred temperature between 20° C. and 65° C. The prolamines are insoluble in the immiscible phase, and precipitate after evaporation of the first solvent, forming a suspension of microspheres. The mixture is cooled to room temperature, washed with a solvent such as petroleum ether to remove the oil, and filtered. The washing and filtering steps are repeated as often as necessary to remove the oil. Generally about three to five washes are needed. The washed microspheres are then dried, generally under vacuum, or frozen and lyophilized.

This method was used to make zein microspheres incorporating solid zinc insulin at two different loadings, 4.8% and 9% (w/w). 0.4 g zein was dissolved in 8.0 ml of 90% ethanol (Pharmco Products, Inc., Norwalk, Conn.) to produce a 5% (w/v) zein (Type F-5000, Freeman Ind., Tuckahoe, N.Y.) solution. 0.02 g of insulin (Calbiochem, Inc., La Jolla, Calif.) was added to the 8.0 ml zein solution to produce microspheres with 4.8% loading. 0.04 g of insulin was added to 8.0 ml zein solution to produce microspheres with 9% loading. The insulin was added as small particles since insulin is insoluble in 90% ethanol. The insulin particles had a mean diameter of 3.2 microns.

The zein/alcohol/insulin mixture was introduced into 150 ml of cold corn oil (Mazola Corn Oil) and homogenized (Virtis Homogenizer, Virtis Corp.) for about 1.5 minutes, then transferred to a larger beaker containing 200 ml of cold corn oil and mixed with a Lightning Mixer at 800 rpm. The mixture was heated to 45° C. for about 45 minutes, then cooled down to room temperature. The resulting microspheres were repeatedly washed with petroleum ether to remove the oil and filtered. They were then dried overnight under vacuum at room temperature.

SEM studies show that zein microspheres produced by this method have a semi-porous structure. They are generally spherical in shape with small pores on the surface. Cross-sections reveal a more porous structure inside. The microspheres have diameters of between one and 20 microns. DSC studies show that the process of encapsulation does not cause denaturation of the zein. However, the type of oil used as the continuous phase may influence the heat of fusion (denaturation) which occurs near 95° C.

EXAMPLE 2

Preparation of Zein Microspheres Containing Rhodamine B, a Small Organic Molecule Soluble in the Zein Solution Zein microparticles incorporating a fluorescent dye, rhodamine B, were prepared according to the procedure described in Example 1, except that 0.008 g rhodamine B (Sigma Chemical Co.) was used in lieu of insulin. Rhodamine B is soluble in the zein solution.

EXAMPLE 3

Preparation of Zein Microspheres Containing Soluble Insulin

Zein microparticles containing insulin were prepared according to the procedure outlined in Example 1, except that the final amount of insulin incorporated was either 17%, 30% or 42% (w/w) and the insulin was dissolved in 90% ethanol-10% water containing 5% zein (w/v), pH 2.5–3.0 (adjusted with 1N HCl). At this pH, insulin remains in solution with the zein. This mixture was then added to the corn oil mixture as described in example 1 to make insulin containing zein microspheres. SEM demonstrated that the microspheres have a dense structure.

EXAMPLE 4

Preparation of Zein-Coated PLA Microspheres containing Rhodamine B

PLA microspheres were prepared as follows: 1 g of PLA was dissolved in 10 ml of methylene chloride, and 0.02 g of rhodamine B was added to the solution. The PLA/rhodamine B solution was dispersed in 400 ml of an aqueous solution containing 1% polyvinylalcohol (DuPont; Wilmington, DE), using a Virtis 23 high shear mixer (The Virtis Co., Gardiner, N.Y.). The dispersion was stirred overnight using a Lightning mixer at 1000 rpm until all of the methylene chloride was evaporated and microspheres formed. The resulting microspheres were washed with water, filtered and dried in a vacuum oven. PLA microspheres containing rhodamine microparticles having diameters ranging from about one to about 10 microns were formed by this method.

The PLA/rhodamine microspheres were coated with zein according to the following procedure: 0.4 g of PLA/rhodamine microspheres were added to 10 ml of a zein solution containing 0.5 g of zein dissolved in 10 ml of 90% ethanol (90:10 ratio of ethanol:water) and stirred with a high shear mixer to form a dispersion. The dispersion was introduced into corn oil with high shear mixing and the corn oil heated according to the procedure outlined in Example 1. The resulting microspheres were cooled, washed with petroleum ether and dried as described in Example 1. When the microspheres were observed under a fluorescent microscope, PLA microspheres with zein coatings were observed. In some instances, several PLA microspheres were observed inside each individual zein microsphere. The diameters of the "composite" microspheres are between 10 and 50 microns.

EXAMPLE 5

Release Kinetics in Vitro of Zein/Insulin Microspheres

Microspheres with two different loadings of insulin, 4.8% and 9% (by weight), were produced as described in Example 1 using particulate insulin, and microspheres with three different loadings, 17%, 30%, and 42%, were produced with soluble insulin as described in example 3.

The release kinetics in vitro were determined by suspending 10 to 20 mg of the zein/insulin microspheres in 2.0 ml phosphate buffered saline (PBS) and incubating the suspension at 37° C. At various time intervals, 1 ml of PBS was decanted and replaced with 1 ml of fresh PBS. Insulin concentration was determined by reverse phase HPLC using a C18 Radial pak column (Waters, Milford, Mass.) with a water acetonitrile gradient.

The microspheres with 9% particulate insulin loading had an initial burst of release of 20% of the drug in a period of about ten hours, with linear release continuing over the next 40 hours. The microspheres with 4.8% particulate insulin loading had an approximate 5% initial release of the drug and linear release over the next 50 hours.

The microspheres with the 17% soluble insulin had approximately 5% release initially, with release rising to 7% after 24 hours, with no further release in vitro for at least the next 90 hours. The microspheres with the 30% soluble insulin had approximately 8% release during the first hour and linear release over the next twenty hours to approximately 15%, with release continuing over at least the next seventy hours. The microspheres with the 42% soluble insulin had approximately 10% release initially, followed by linear release over the next ninety hours.

Samples collected at various time points were run on SDS-PAGE to check for degradation of the insulin. No degradation was observed.

EXAMPLE 6

Bioactivity of Zein/Insulin Microspheres in Vivo

A reproducible bioassay for insulin release is the measurement of blood glucose of diabetic rats following injection of the microspheres subcutaneously. Diabetes is induced in female Sprague-Dawley rats (Taconic Farms, N.Y.) by intravenously injecting 65 mg/kg streptozotocin (Upjohn Co., Kalamazoo, Mich.) in 0.1M citrate buffer, pH 4.5.

12.0 mg of 17% (w/w) loading zein/insulin microspheres prepared as described in Example 3, in 1 ml normal saline, was administered to the rats. An equivalent dose of soluble (not encapsulated) insulin was injected into other rats as a control. The results of this experiment showed some differences in the length of biological activity between zein/insulin microspheres and soluble insulin injected subcutaneously. The microspheres released insulin over a longer period of time and therefore resulted in a longer period of bioactivity than the soluble insulin.

EXAMPLE 7

Preparation of Fatty Acid Modified Zein Microspheres and In Vitro Release Kinetics Zein was modified with either hexanoic anhydride (C6), octanoic anhydride (C8), decanoic anhydride (C10) or lauric anhydride (C12). The zein and the specific anhydride were added to a medium consisting of 80% ethanol and 20% sodium borate (20 mM pH 9.0) and allowed to react with stirring at 37° C. for 2 hours with a five fold molar excess of anhydride. The pH was maintained by slow addition of sodium hydroxide during the course of the reaction. After two hours, the solutions were acidified to pH 3.0 by addition of 37% HCl, and then extracted five times with several volumes of petroleum ether to remove the free fatty acids. The material was dialyzed overnight against $2 \times 15$ L of distilled water, frozen at $-80°$ C. and lyophilized.

Modified zein microspheres containing insulin were prepared according to the procedure outlined in Example 3. The amount of insulin incorporated was 17% (w/w). The modified zeins were dissolved in 90% ethanol, 10% water, pH 2.5-3.0, to a final concentration of 5%.

Figure 2A:
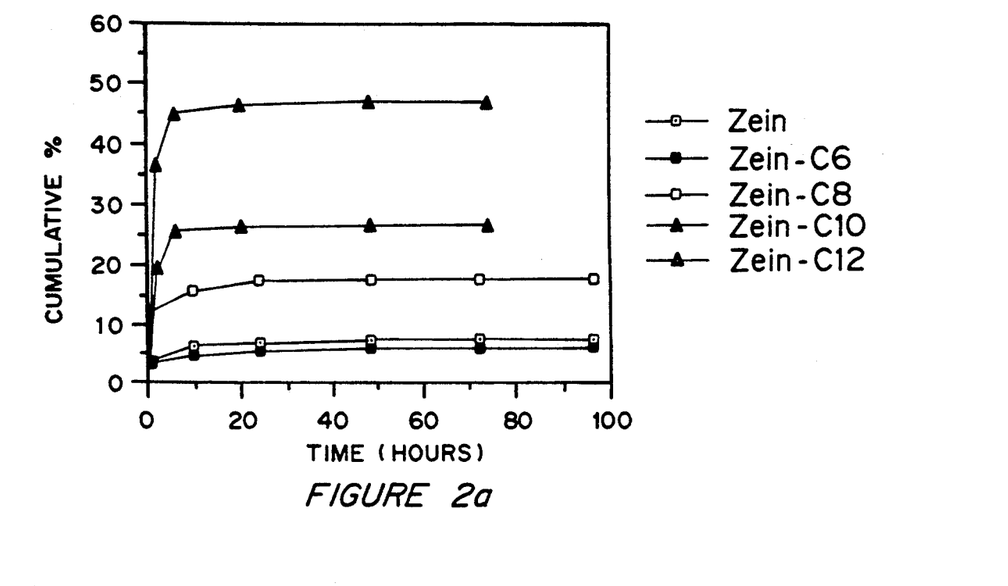

The in vitro release kinetics of insulin from zein-C6, zein-C8, zein-C10 and zein-C12 microspheres were determined. The release kinetics were determined as in Example 5 and are shown in FIG. 2A.

EXAMPLE 9

Preparation of Deamidated Zein and Deamidated Zein Modified with Fatty Acid Microsphere Solution Formulation and Release Kinetics in Vitro Deamidated zein was prepared as follows: a mixture of 5% (w/v) zein (Freeman Ind., Inc.) in 70% aqueous ethanol was titrated to pH 1.0 with 37% HCl (final HCl concentration approximately 0.12N) and incubated at 37° C. for 96 hours. The reaction was monitored with an ammonia electrode and the degree of deamidation determined. After 96 hours the reaction mixture was neutralized with 1M ammonium carbonate to terminate deamidation. The deamidated zein was recovered by dialysis against distilled water in 6000 molecular weight cutoff dialysis tubing (Spectrum). The deamidated zein precipitated during dialysis. The material was frozen at $-80°$ C. and lyophilized in a shelf lyophilizer (The Virtis, Co., Gardiner, N.Y.)

Deamidated zein was modified with either hexanoic anhydride (C6), octanoic anhydride (C8), decanoic anhydride (C10) or lauric anhydride (C12). The deamidated zein and the specific anhydride were added to a medium consisting of 80% ethanol and 20% sodium borate (20 mM pH 9.0) and allowed to react with stirring at 37° C. for 2 hours with a five fold molar excess of anhydride. The pH was maintained by slow addition of sodium hydroxide during the time course of the reaction. After two hours, the solutions were acidified to pH 3.0 by addition of 37% HCl, and then extracted five times with several volumes of petroleum ether to remove the free fatty acids. The material was dialyzed overnight against 2×15 L of distilled water, frozen at −80° C. and lyophilized.

Deamidated zein and fatty acid modified deamidated zein microspheres containing insulin were prepared according to the procedure outlined in Example 3. The amount of insulin incorporated was 17% (w/w). The deamidated zein and the fatty acid modified deamidated zein were dissolved in 90% ethanol in water to a final concentration of 5% (w/w). Insulin was added and the pH adjusted to 2.5-3.0.

Figure 2B:
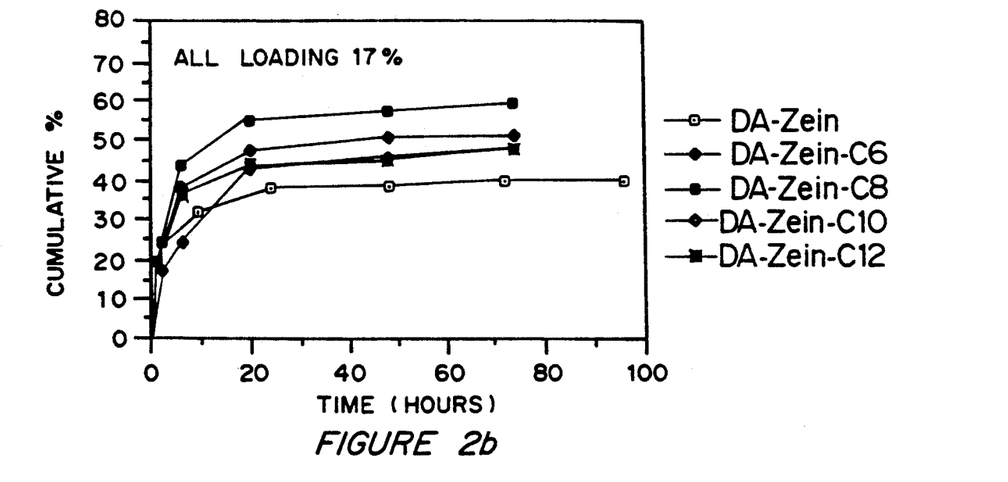

The in vitro release kinetics of insulin from deamidated zein, deamidated zein-C6, deamidated zein-C8, deamidated zein-C10 and deamidated zein-C12 were determined. The release kinetics were monitored as in Example 5 and are shown in FIG. 2B.

EXAMPLE 10

In Vivo Activity of Zein-C6 and Deamidated Zein Insulin Microspheres

The insulin containing microspheres formed from zein-C6 and deamidated zein prepared in examples 8 and 9 were tested for bioactivity as described in Example 6. Blood glucose levels of rats injected subcutaneously indicated that release occurs over an extended period of time and reduces the blood glucose levels.

EXAMPLE 11

Preparation of PLA/Zein Composite Microspheres

Zein microspheres incorporating the fluorescent dye, Rhodamine B, were prepared as described in Example 2. The microspheres had diameters in the range of between one and 12 microns. These microspheres were incorporated into PLA microspheres as follows: 0.5 g PLA (L-104, Boerhinger Ingelheim, FRG) was dissolved in 10 ml of methylene chloride. 52 mg of the rhodamine B zein microspheres were added to the polymer solution. Zein is insoluble in pure methylene chloride. This mixture was sonicated on ice using a Virsonic 300 Ultrasonic probe (Virtis Inc., Gardiner, N.Y.) for one minute. The suspension was then placed in a 10 ml gas tight syringe. 100 ml of 100% ethanol was added to a round container (8 cm by 6 cm) and frozen in a liquid nitrogen bath. The frozen ethanol was then covered by a layer of liquid nitrogen. The polymer suspension was extruded from the syringe via a syringe pump a rate of 2 ml/min into an ultrasonic nozzle (Model 8700-48MS, Sonotek Corp., Poughkeepsie, N.Y.) that was placed 8 cm above the liquid nitrogen/frozen ethanol solution. The nozzle atomized the suspension into droplets which froze immediately upon contacting the liquid nitrogen. The container was placed in −80° C. freezer to evaporate the liquid nitrogen and thaw the ethanol. The methylene chloride was extracted into the cold ethanol, hardening the microspheres. After 24 hours, 200 ml of hexane precooled to −80° C. was added to the container to further extract the methylene chloride. The microspheres were kept in the freezer for an additional 24 hours, after which they were filtered and washed in 100 ml of cold hexane. The microspheres were then vacuum dried at room temperature for 24 hours.

Under light microscopy, the spheres were round and had diameters ranging from 30-35 microns. The microspheres were observed with an Olympus (Lake Success, NY) BH2 microscope equipped for epi-illumination fluorescent microscopy with a 100 W high pressure mercury lamp with the appropriate filters for the visualization of rhodamine B.

The particles fluoresced at a greater intensity than the background. It was possible to detect discrete fluorescent particles inside of individual PLA microspheres. The PLA microspheres were then redissolved in methylene chloride and a sample of this solution was examined. Discrete zein rhodamine B microspheres were observed, indicating that the fluorescence in the PLA microspheres was due to the intact zein rhodamine B microspheres and not rhodamine B which had leaked out of the zein into the PLA during the fabrication procedure.

EXAMPLE 12

Preparation of Microspheres with a 50:50 Mixture of Zein and Deamidated Zein Containing Insulin Microspheres containing insulin were prepared as described in example 3, except that 0.2 g of zein and 0.2 g of deamidated zein were dissolved in 8.0 ml of 90% ethanol-10% water, pH 2.5-3.0, adjusted with 1.0N HCl. The amount of insulin incorporated was 17% (w/w).

Figure 3:
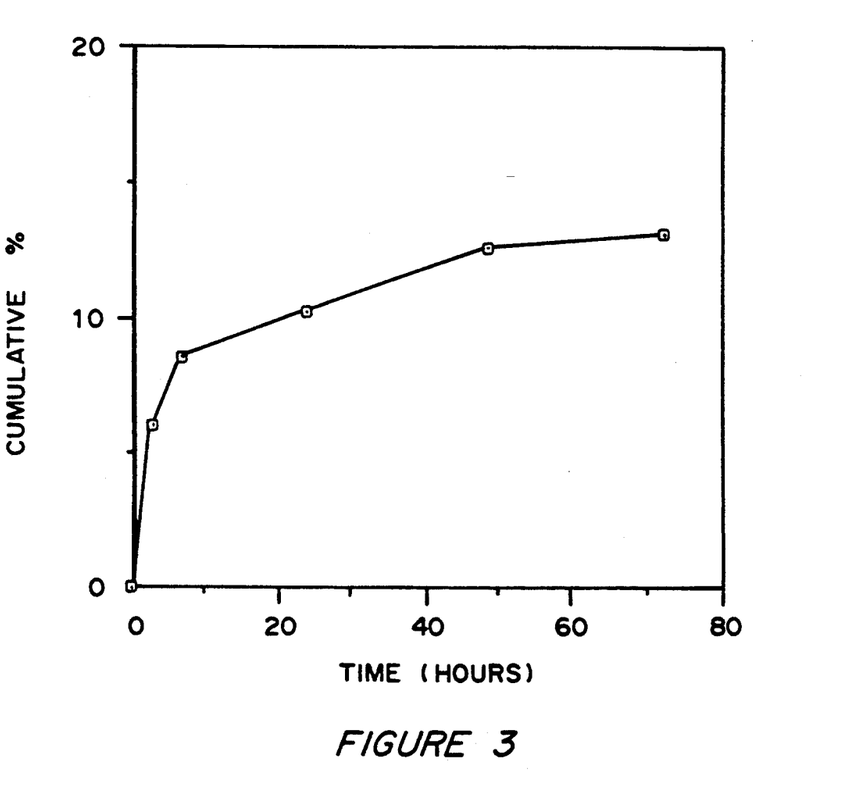
FIG. 3 is a graph of the % cumulative release of insulin from microspheres formed of a blend of zein and deamidated zein (50:50) over time (hours).

The in vitro release kinetics shown in FIG. 3 demonstrate that approximately 10% of the insulin was released over the first ten hours, and another 5% over the next 60 hours.

Modifications and variations of the present invention will be obvious to those skilled in the art from the foregoing detailed description. Such modifications and variations are intended to come within the scope of the appended claims.

We claim:

1. A method for producing protein microspheres comprising the steps of:
   a) contacting a prolamine solution, wherein the prolamine solution contains at least one type of prolamine and a compound to be incorporated into the microspheres, with a second liquid, wherein the second liquid is of limited miscibility with the prolamine solvent such that the second liquid does not form a stable homogeneous solution with the prolamine solvent and does not dissolve the prolamine, in a ratio of prolamine solution to second liquid of at least 1:20, to form a prolamine-non-solvent mixture;
   b) agitating the prolamine-non-solvent mixture to form a dispersion of the prolamine solution in the second liquid at a temperature of less than about 65° C.; and
   c) removing the prolamine solvent to form stable prolamine microspheres without crosslinking or heat denaturation.

2. The method of claim 1 wherein the prolamine is selected from the group consisting of zein, gliadin, hordein and kafirin.

3. The method of claim 1 comprising, prior to forming the prolamine solution, modifying the prolamine to enhance or alter one of the properties of thermal stability, surface reactivity, lipophilicity, molecular weight, charge, shear stability or resistance to proteases.

4. The method of claim 3 wherein the prolamine is chemically modified.

5. The method of claim 4 wherein the prolamine is deamidated with acid.

6. The method of claim 4 wherein the prolamine is chemically modified by esterification with a fatty alcohol.

7. The method of claim 4 wherein the prolamine is chemically modified by acylation with a fatty anhydride.

8. The method of claim 4 wherein the prolamine is chemically modified by coupling amino acids, peptides, or proteins to the prolamine.

9. The method of claim 3 wherein the prolamine is cleaved enzymatically into smaller molecular weight fragments.

10. The method of claim 1 wherein the prolamine solvent is selected from the group consisting of alcohols, ketones, and amide solvents, aqueous mixtures of alcohols, ketones, and amide solvents containing no more than 60% water, solutions having pH of 10 or more, solutions having pH of 2 or less, aqueous solutions of inorganic salts in concentrations of from about 1.0 to about 6N, and binary alcohols and halogenated hydrocarbons or polyols, and combinations thereof.

11. The method of claim 1 wherein the second liquid is selected from the group consisting of oils, hexane, heptane, dodecane, high boiling point petroleum ether, and combinations thereof.

12. The method of claim 1 further comprising a compound selected from the group consisting of surfactants and binders.

13. The method of claim 1 further comprising mixing a non-protein polymer with the prolamine containing incorporated drug to form composite prolamine microspheres.

14. The method of claim 13 wherein the polymer is selected from the group consisting of poly(lactic acid)s, poly(glycolic acid)s, polyanhydrides, polyorthoesters, polycaprolactones, polyphosphazenes, polyhydroxybutyrates, polyamides, blends and copolymers thereof.

15. The method of claim 1 further comprising adding particles insoluble in the prolamine solution to form prolamine coated particles.

16. The method of claim 15 wherein the particles are selected from the group consisting of microspheres and microcapsules.

17. The method of claim 15 wherein the particles are formed of a material selected from the group consisting of proteins, inorganic salts, polysaccharides, metals and non-protein polymers.

18. The method of claim 1 wherein the compound is selected from the group of biologically active compounds consisting of pharmaceuticals, pesticides, nutrients, imaging agents, and chelating agents.

19. The method of claim 1 wherein the compound is soluble in the prolamine solution.

20. The method of claim 1 wherein the compound is insoluble in the prolamine solution.

* * * * *